US011540934B2

(12) United States Patent
Marko

(10) Patent No.: US 11,540,934 B2
(45) Date of Patent: Jan. 3, 2023

(54) ADJUSTABLE BACK BRACE AND METHODS FOR USE THEREOF

(71) Applicant: BRANDEIS UNIVERSITY, Waltham, MA (US)

(72) Inventor: Ingrid Marko, Waltham, MA (US)

(73) Assignee: Brandeis University, Waltham, MA (US)

( * ) Notice: Subject to any disclaimer, the term of this patent is extended or adjusted under 35 U.S.C. 154(b) by 256 days.

(21) Appl. No.: 16/608,092

(22) PCT Filed: Apr. 27, 2018

(86) PCT No.: PCT/US2018/029896
§ 371 (c)(1),
(2) Date: Oct. 24, 2019

(87) PCT Pub. No.: WO2018/201013
PCT Pub. Date: Nov. 1, 2018

(65) Prior Publication Data
US 2020/0093629 A1    Mar. 26, 2020

Related U.S. Application Data

(60) Provisional application No. 62/491,577, filed on Apr. 28, 2017.

(51) Int. Cl.
*A61F 5/00* (2006.01)
*A61F 5/02* (2006.01)

(52) U.S. Cl.
CPC .............. *A61F 5/024* (2013.01); *A61F 5/022* (2013.01)

(58) Field of Classification Search
CPC .... A61F 5/024; A61F 5/02; A61F 5/01; A61F 5/055; A61F 5/028; A61F 5/026;
(Continued)

(56) References Cited

U.S. PATENT DOCUMENTS 3,420,230 A * 1/1969 Ballard ................... A61F 5/024
602/36
4,470,417 A * 9/1984 Gruber .................... A61F 5/028
607/108

(Continued)

OTHER PUBLICATIONS

Aetna. Idiopathic scoliosis Policy Bulletin. (2016) Available online at http://www.aetna.com/cpb/medical/data/300_399/0398.html.
(Continued)

*Primary Examiner* — Adam Baker
(74) *Attorney, Agent, or Firm* — Quarles & Brady LLP

(57) ABSTRACT

An adjustable back brace configured to aid in the correction of spinal curvature during a treatment period of a patient is provided. In some aspects, the adjustable back brace comprises a rod, an inferior segment, and a superior segment. The inferior segment is configured to stabilize a pelvic region of the patient. The superior segment is configured to apply pressure to one of a first lateral side and a second lateral side of the patient, proximate a thoracic region of the patient to provide a corrective force on the spinal curvature of the patient. The superior segment is also selectively adjustable to be selectively moved and fixedly positioned in a plurality of positions along at least one of the lateral direction or the vertical direction, wherein the plurality of positions are designed for periodic adjustment of the corrective force on the spinal curvature during the treatment period.

12 Claims, 6 Drawing Sheets

(58) Field of Classification Search
CPC ...... A61F 5/03; A61F 5/00; A61F 5/28; A61F 5/0102; A61F 5/30; A61F 5/32; A61F 5/022; A61F 13/14; A61H 1/0292; A61H 1/0218; A61H 1/008
USPC .......................................................... 602/19
See application file for complete search history.

(56) References Cited

U.S. PATENT DOCUMENTS

| | | | | |
|---|---|---|---|---|
| 4,658,807 | A * | 4/1987 | Swain | A47C 31/126 602/19 |
| 5,086,757 | A * | 2/1992 | Lestini | A61F 5/055 602/17 |
| 5,437,614 | A * | 8/1995 | Grim | A61F 5/022 602/19 |
| 5,449,338 | A * | 9/1995 | Trudell | A61F 5/024 602/19 |
| 6,899,689 | B1 * | 5/2005 | Modglin | A61F 5/022 128/869 |
| 8,005,651 | B2 | 8/2011 | Summit | |
| 8,613,716 | B2 | 12/2013 | Summit | |
| 8,986,234 | B2 | 3/2015 | Summit | |
| 2004/0167448 | A1 | 8/2004 | Heffez | |
| 2006/0079821 | A1 * | 4/2006 | Rauch | A61F 5/022 602/19 |
| 2009/0137934 | A1 * | 5/2009 | Seon | A61F 5/0123 602/19 |
| 2012/0157901 | A1 * | 6/2012 | Galante | A61G 5/12 602/19 |
| 2015/0018736 | A1 | 1/2015 | Perez et al. | |

OTHER PUBLICATIONS

American Association of Neurological Surgeons. Scoliosis. (2017) Available online at www.aans.org/Patient%20Information/Conditions%20and%20Treatments/Scoliosis.aspx.

Daffner, S. D., et al. (2010). Geographic and Demographic Variability of Cost and Surgical Treatment of Idiopathic Scoliosis. Spine, 35(11), 1165-1169. doi:10.1097/brs.0b013e3181d88e78.

Hooper, C. et al. (2003) The charleston bending brace: an orthotist's guide to scoliosis management. The Charleston Bending Brace Foundation 1990.

International Searching Authority, International Search Report and Written Opinion for application PCT/US2018/029896, dated Jul. 13, 2018.

Scoliosis.com Types of braces for scoliosis, (published Jul. 11, 2007) Retrieved from http://www.iscoliosis.com/articles-brace_types.html on Nov. 4, 2019.

Stokes, I. et al, (2006). Biomechanics of scoliosis. Encyclopedia of Medical Devices and Instrumentation. (2). John Wiley & Sons, Inc.

* cited by examiner

ADJUSTABLE BACK BRACE AND METHODS FOR USE THEREOF

CROSS-REFERENCE TO RELATED APPLICATIONS

This application represents the U.S. National Stage of International Application No. PCT/US2018/029896, filed Apr. 27, 2018, which is based on, claims priority to, and incorporates herein by reference in its entirety for all purposes, U.S. Provisional Patent Application Ser. No. 62/491,577, filed Apr. 28, 2017, and entitled "Adjustable Back Brace and Methods for Use Thereof."

STATEMENT REGARDING FEDERALLY SPONSORED RESEARCH

Not applicable.

BACKGROUND

The field of the disclosure relates to braces used to correct scoliosis of the spine.

Scoliosis is a spine disorder that affects 2-3% of the population (approximately 9 million people) in the United States. Scoliosis is defined as idiopathic and can be caused by either genetics or environment. The popularity of unhealthy diets and decreases in sports activities among children results in deformed bones and spinal structure. It is important to be treating all cases of scoliosis to prevent further declines in health. Treatment for scoliosis can be surgical or nonsurgical (bracing). If left to natural development, the spinal curve may progress to a point that surgery is required for the patient. Severe curvature(>50° will induce physical deformities and health risks that can affect heart and lung function.

Braces remain as custom products that have long production times, which can lead to ineffective or incorrect treatment. Currently, the Boston and Charleston back braces are being used to treat moderate to severe scoliosis in children and teens aged 8-16 years old. These braces help prevent curvature in the spine from progressing, but are usually made once per patient, and can therefore have a lead time of a few weeks up to a few months. As such, these braces cannot readily offer an effective medical treatment. Any time spent without treatment can have negative effects on a growing child and may limit the capability of a back brace to provide optimal treatment. Accordingly, this long lead time is undesirable.

The main people affected by scoliosis are young girls and boys with a ratio of 7:1, respectively. Traditional braces do not take into account the high growth rates of children during this time period. As such traditional braces, which are typically not updated or replaced during a treatment period, can be outgrown by the patient during the treatment period. When the patient outgrows their brace, it can lead to an incorrect application of corrective forces on the spine, resulting in the brace being ineffective, or in some instances, actually leading to a negative progression (i.e., an increase in spinal curvature).

Due to the extensive lead time and lack of adjustability, braces currently used during treatment have a success rate of 30%, defined by spinal curves that do not increase more than 6° throughout the treatment period. The low success rate observed with traditional back braces has a negative impact on the health and the quality of life of children, mainly young girls, with scoliosis and has been associated with the onset of depression.

Additionally, the cost of treatment for scoliosis can vary significantly. A single back brace can cost approximately two-thousand dollars. The total cost per patient for non-operative treatment for scoliosis during a 5-year period can be up to twenty-thousand dollars including the brace, examinations, and pain medications. Surgery is generally a last resort for spinal curves that progress above a 40° curve angle and cannot be treated with a brace. Surgical correction of severe spinal curves can raise the treatment cost to one hundred and fifty thousand dollars.

Therefore, it would be desirable to have a brace capable of being adjusted periodically throughout the treatment period, which could also be made commercially to improve availability and decrease the required lead time.

SUMMARY

The present disclosure provides an adjustable back brace that is capable of providing corrective forces to the spine of a patient. The adjustable back brace is additionally capable of being periodically adjusted throughout a treatment period of the patient to account for growth of the patient, as well as changes in the spinal curvature of the patient, throughout the treatment period. Thus, the adjustable back brace provided herein improves treatment efficacy, while reducing the overall cost of treatment.

In accordance with one aspect of the disclosure, a back brace configured to aid in the correction of spinal curvature during a treatment period of a patient is provided. The back brace comprises a rod, an inferior segment, and a superior segment. The rod is configured to extend along a vertical direction oriented along the patient. The inferior segment is coupled to the rod and is configured to extend in a lateral direction to at least partially wrap around and conform to the patient during use. The inferior segment is further configured to apply pressure to both a first lateral side and a second lateral side of the patient proximate a pelvic region of the patient, thereby stabilizing the pelvic region of the patient relative to the rod. The superior segment is adjustably coupled to the rod above the inferior segment and is configured to extend in a lateral direction to at least partially wrap around and conform to the patient during use. The superior segment is further configured to apply pressure to one of the first lateral side and the second lateral side of the patient, proximate a thoracic region of the patient, to provide a corrective force on the spinal curvature of the patient. The superior segment is selectively adjustable, such that the superior segment can be selectively moved and fixedly positioned in a plurality of positions along at least one of the lateral direction or the vertical direction, wherein the plurality of positions are designed for periodic adjustment of the corrective force on the spinal curvature during the treatment period.

In some aspects, the back brace can further comprise a middle segment adjustably coupled to the rod between the inferior segment and the superior segment and configured to at least partially wrap around and conform to the patient during use. The middle segment can further be configured to apply pressure to another one of the first lateral side and the second lateral side of the patient, proximate a lumbar region of the patient, opposite the one of the first lateral side and the second lateral side having pressure applied thereon by the superior segment to provide an additional corrective force on the spinal curvature of the patient. The middle segment can be selectively adjustable, such that the middle segment can be selectively moved and fixed positioned in another plurality of positions along at least one of the lateral direction of the vertical direction, wherein the another plurality of positions are designed for periodic adjustment of the additional corrective force on the spinal curvature of the patient during the treatment period.

In accordance with another aspect of the disclosure, a back brace configured to aid in the correction of spinal curvature during a treatment period of a patient is provided. The back brace comprises a rod, an inferior segment, a superior segment, and a middle segment. The rod is configured to extend along a vertical direction oriented along a patient. The inferior segment is coupled to the rod, extends in a lateral direction from the rod, and is configured to at least partially wrap around and conform to the patient during use. The inferior segment is further configured to apply pressure to both a first lateral side and a second lateral side of the patient proximate a pelvic region of the patient, thereby stabilizing the pelvic region of the patient relative to the rod. The superior segment is adjustably coupled to the rod above the inferior segment, extends in a lateral direction from the rod, and is configured to at least partially wrap around and conform to the patient during use. The superior segment is further configured to apply pressure to one of the first lateral side and the second lateral side of the patient, proximate a thoracic region of the patient, to provide a first corrective force on the spinal curvature of the patient. The middle segment is adjustably coupled to the rod between the inferior segment and the superior segment and is configured to at least partially wrap around and conform to the patient during use. The middle segment is further configured to apply pressure to another one of the first lateral side and the second lateral side of the patient, proximate a lumbar region of the patient, opposite the one of the first lateral side and the second lateral side having pressure applied thereon by the superior segment to provide a second corrective force on the spinal curvature of the patient.

In some aspects, each of the superior segment and the middle segment can be selectively adjustable, such that the superior segment can be selectively moved and fixedly positioned in a first plurality of positions along at least one of the lateral direction or the vertical direction and the middle segment can be selectively moved and fixedly positioned in a second plurality of positions along at least one of the lateral direction or the vertical direction. The first plurality of positions and the second plurality of positions can be designed for periodic adjustment of the first corrective force and the second corrective force on the spinal curvature during the treatment period.

In some aspects, at least one of the inferior segment, the middle segment, and the superior segment can include a removable pad on an interior surface, wherein the removable pad has a thickness selected to provide an anterior-posterior spinal curvature correction force. At least one of the inferior segment, the middle segment, and the superior segment can include an adjustment mechanism, configured to adjustably couple a corresponding one of the inferior segment, the middle segment, and the superior segment to the rod. The adjustment mechanism can comprise an adjustment plate having a plurality of adjustment apertures, the rod can include a plurality of connection apertures, and the adjustment plate can be configured to be coupled to the rod by using at least one fastener to couple at least one adjustment aperture to at least one connection aperture. The plurality of adjustment apertures can be arranged in a matrix having a plurality of horizontal rows and a plurality of vertical rows, such that the matrix is configured to allow for the selective adjustability of the corresponding one of the inferior segment, the middle segment, and the superior segment in at least one of the lateral direction or the vertical direction.

In some aspects, each of the inferior segment, the middle segment, and the superior segment can include a rear portion extending laterally away from the rod and a pair of opposed arm portions extending away from opposing lateral sides of the rear portion in an anterior direction. Each of the inferior segment, the middle segment, and the superior segment can include a tension mechanism configured to pull the pair of opposed arm portions toward each other.

In accordance with another aspect of the disclosure, a method for correcting spinal curvature of a patient with a back brace including a rod, an inferior segment coupled to the rod, and a superior segment adjustably coupled to the rod above the inferior segment is provided. The method comprises securing the inferior segment to a pelvic region of the patient to stabilize the pelvic region of the patient relative to the rod. The method further comprises placing the superior segment around a thoracic region of the patient. Subsequent to placing the superior segment around the thoracic region of the patient, the method further comprises rigidly coupling the superior segment to the rod in a desired alignment, relative to the inferior segment. Subsequent to rigidly coupling the superior segment to the rod in the desired alignment, the method further comprises tightening the superior segment around the thoracic region of the patient, thereby applying pressure to one of the first lateral side and the second lateral side of the thoracic region of the patient. The desired alignment is predetermined to apply a corrective force to the spinal curvature of the patient when the superior segment is tightened around the thoracic region of the patient.

In some aspects, the back brace can additionally include a middle segment adjustably coupled to the rod between the inferior segment and the superior segment. The method can further comprise placing the middle segment around a lumbar region of the patient. Subsequent to placing the middle segment around the lumbar region of the patient, the method can further comprise rigidly coupling the middle segment to the rod in a desired middle segment alignment, relative to the inferior segment. Subsequent to rigidly coupling the middle segment to the rod in the desired middle segment alignment, the method can further comprise tightening the middle segment around the lumbar region of the patient, thereby applying pressure to one of the first lateral side and the second lateral side of the lumbar region of the patient opposite the one of the first lateral side and the second lateral side of the patient having pressure applied thereon by the superior segment. The desired middle segment alignment can predetermined to apply a secondary corrective force to the spinal curvature of the patient when the middle segment is tightened around the lumbar region of the patient.

In some aspects, at least one of the middle segment and the superior segment can be selectively adjustable, such that the at least one of the middle segment and the superior segment can be selectively moved in either of a lateral direction and a vertical direction, with respect to the inferior segment, allowing for periodic adjustment of the back brace during the treatment period.

The foregoing and other aspects and advantages of the invention will appear from the following description. In the description, reference is made to the accompanying drawings which form a part hereof, and in which there is shown by way of illustration a preferred embodiment of the inven-

DETAILED DESCRIPTION OF THE INVENTION

Figure 1:
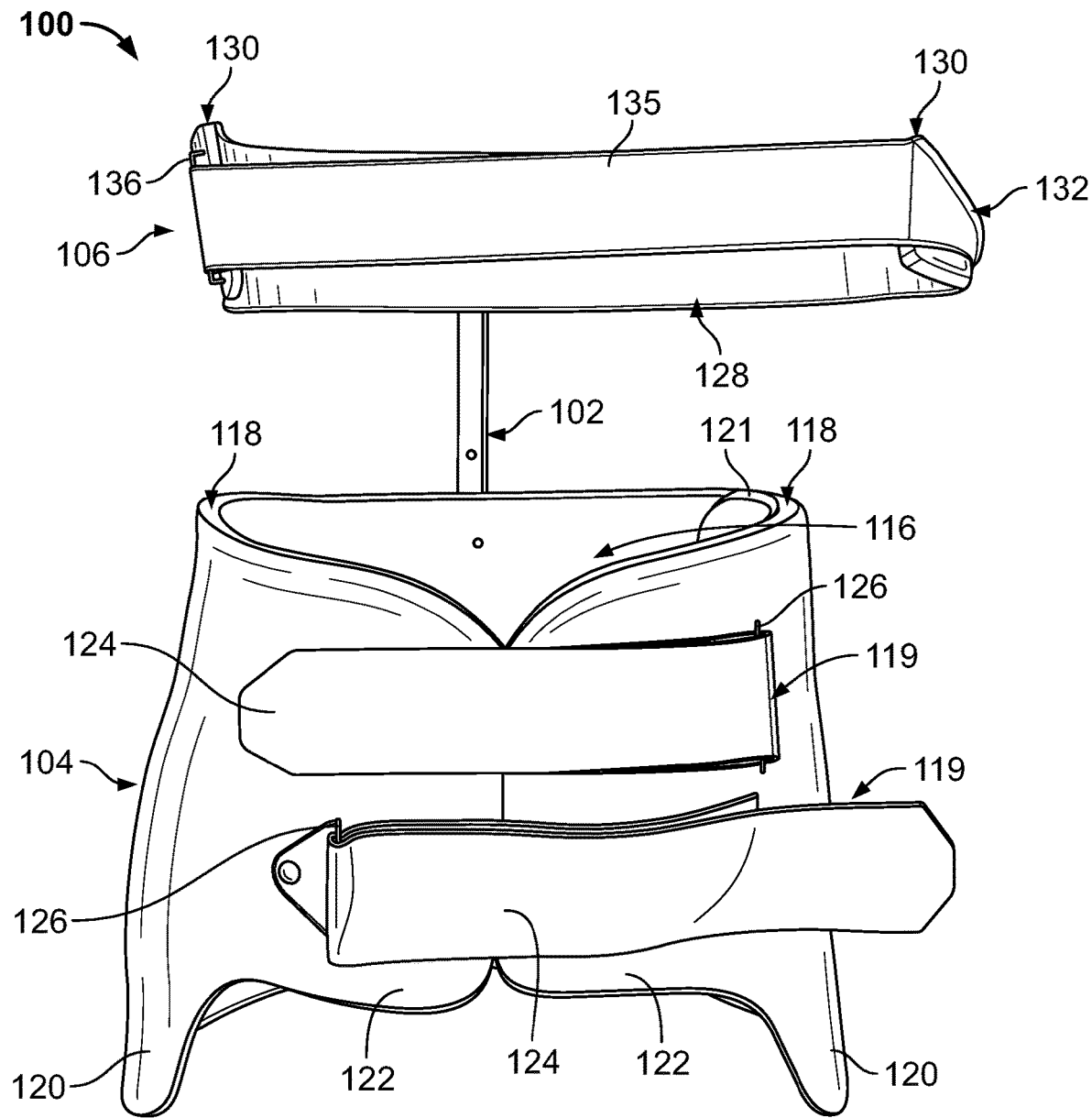
FIG. 1 is a front elevational view of an adjustable back brace in accordance with the present disclosure.
Figure 2:
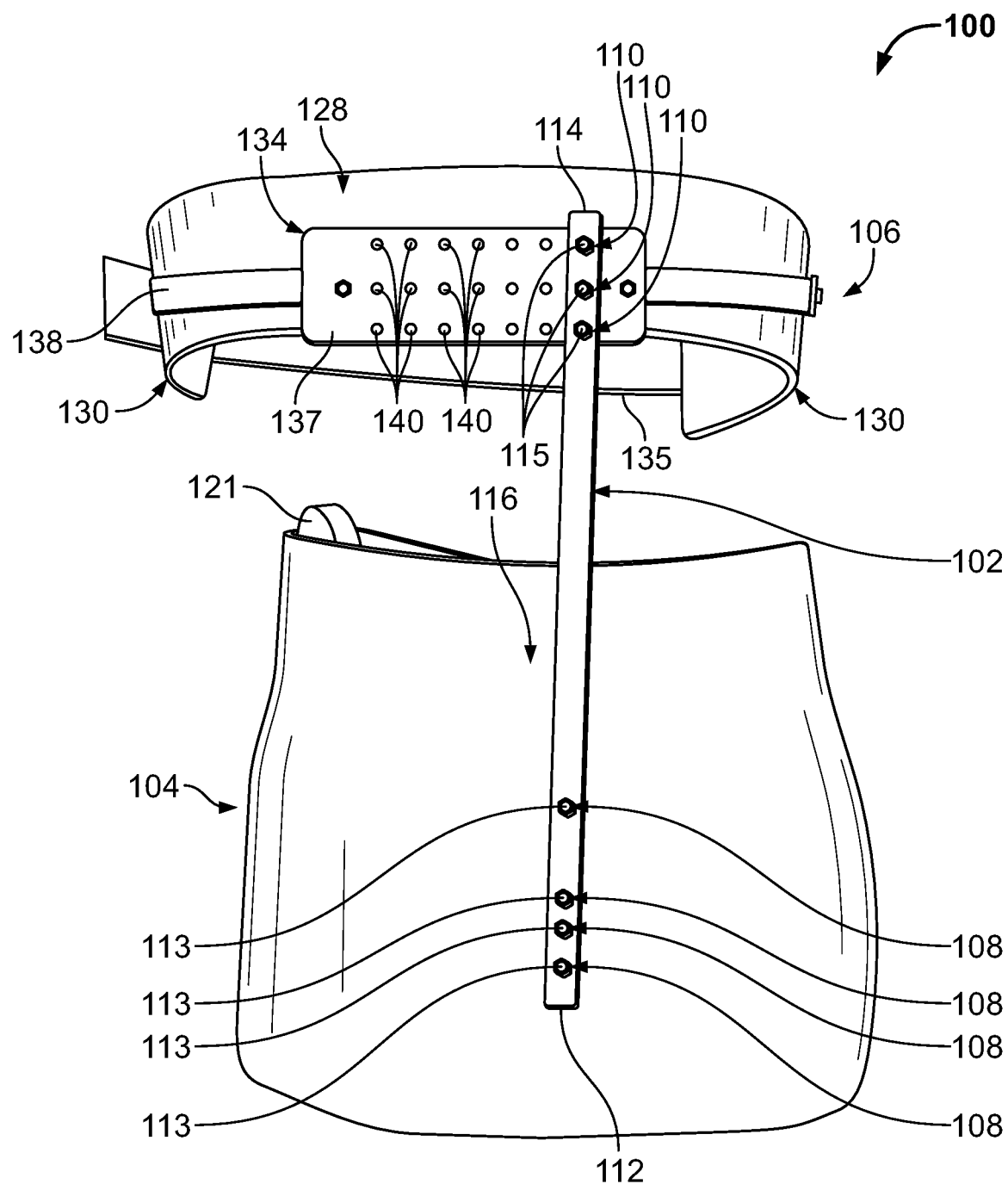
FIG. 2 is a back elevational view of the adjustable back brace of FIG. 1.
Figure 3:
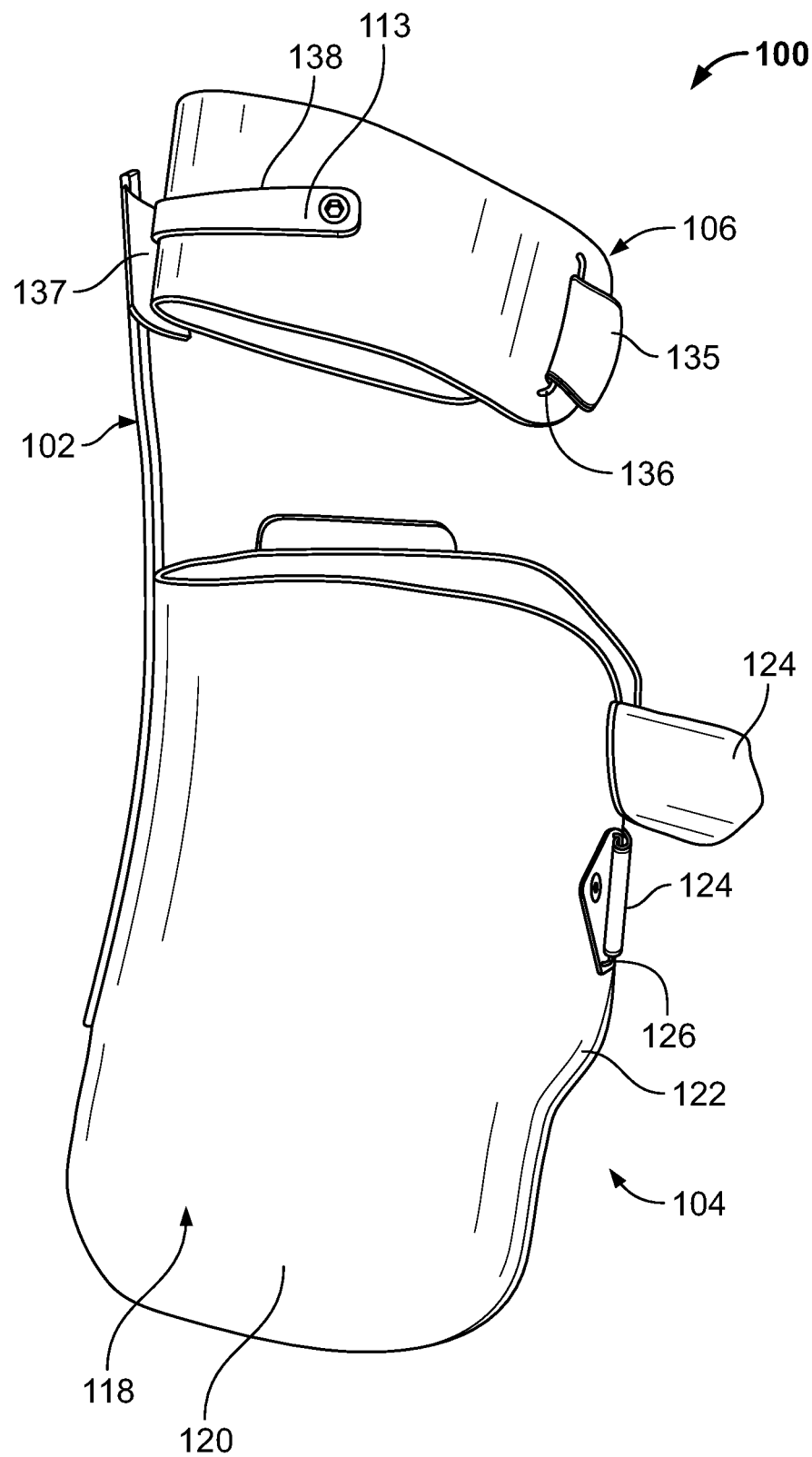
FIG. 3 is a left side elevational view of the adjustable back brace of FIG. 1.

Referring now to FIGS. 1-3, a non-limiting example of a back brace 100 is illustrated for correcting scoliosis, or spinal curvature, of a patient. The adjustable back brace 100 includes a rod 102, an inferior segment 104, and a superior segment 106.

As best illustrated in FIG. 2, the rod 102 is configured to extend along a vertical direction oriented along a patient. The rod 102 includes a plurality of inferior segment connection apertures 108 and a plurality of superior segment connection apertures 110. The plurality of inferior segment connection apertures 108 are disposed proximate an inferior end 112 of the rod 102 and are further coupled to the inferior segment 104 of the back brace 100 using a plurality of fasteners 113. As illustrated, the rod 102 includes four inferior segment connection apertures 108. In some instances, the rod 102 can include less than four inferior segment connection apertures 108 to simplify the design of the back brace 100. In some other instances, the rod 102 can include more than four inferior segment connection apertures 108 to provide additional rigidity and adjustability, as desired.

The superior segment connection apertures 110 are disposed proximate a superior end 114 of the rod 102 and are further coupled to the superior segment 106 of the back brace 100 by a plurality of fasteners 115. As illustrated, the rod 102 includes three superior segment connection apertures 110. In some instances, the rod 102 can include more than three superior segment connection apertures 110 to provide additional vertical adjustability. For example, in some instances, the rod 102 can include four, five, six, or any other suitable number of superior segment connection apertures 110.

Referring back to FIGS. 1-3, the inferior segment 104 includes a rear portion 116, a pair of opposed arm portions 118, and tension mechanism 119. As illustrated, the rear portion 116 and the pair of opposed arm portions 118 are formed together as a single unitary piece, which is configured to wrap around and conform to a pelvic region of the patient during use, as will be described below.

The rear portion 116 is coupled to the rod 102 and extends both laterally away from the rod 102 and in an inferior direction, extending beyond the inferior end 112, with respect to the rod 102. The rear portion 116 is configured to conform to the back of the pelvic region of the patient. The pair of opposed arm portions 118 extend from opposing lateral sides of the rear portion 116. The pair of opposed arm portions 118 are each configured to conform to a corresponding lateral side of the pelvic region of the patient. The pair of opposed arm portions 118 each include a lateral section 120 and an anterior section 122. The lateral sections 120 extend from the opposing lateral sides of the rear portion 116 in a generally anterior direction. Additionally, the lateral sections 120 extend along a vertical length of the rear portion 116, such that the lateral sections 120 each have a vertical length substantial similar to the vertical length of the rear portion 116.

Either of the pair of opposed arm portions 118 may further include a removable pad 121 extending around an inner portion of the corresponding arm portion 118. In some instances, the removable pad 121 may be included to improve comfortability of the back brace 100. In some other instances, the removable pad 121 may have a thickness selected to provide a desired anterior-posterior spinal curvature correction force. For example, the thickness of the removable pad 121 may be thicker toward a posterior end of the removable pad 121 and thinner toward an anterior end of the removable pad 121 to provide an anteriorly-directed spinal curvature correction force. In some instances, the removable pad 121 may comprise a combination of a stiff foam layer and a soft foam layer. For example, the stiff foam layer may be disposed adjacent the corresponding arm portion 118 to provide the desired anterior-posterior spinal curvature correction force, and the soft foam layer may be disposed adjacent the patient to increase comfortability. In some instances, the stiff foam layer may comprise [INVENTOR: Please provide a few possible materials for the stiff foam layer of the removable pad.] or any other suitable material. In some instances, the soft foam layer may comprise [INVENTOR: Please provide a few possible materials for the soft foam layer of the removable pad.] or any other suitable material.

In some instances, the removable pad 121 can further comprise a heating and/or a cooling layer, which can be configured to either retain heat within the back brace 100, or transfer heat out of the back brace 100, as desired.

The anterior sections 122 each extend from an anterior end of the corresponding lateral sections 120 in a generally medial direction. The anterior sections 122, however, only extend along a portion of the lateral sections 120. Specifically, the anterior sections 122 each extend from a superior end of the corresponding lateral section 120 and terminate proximate a center of the corresponding lateral section 120, such that each of the anterior sections 122 has a shorter vertical length than the vertical length of the corresponding lateral sections 120.

The tension mechanisms 119 are each selectively coupled to both of the anterior sections 122 of the pair of opposed arm portions 118. The tension mechanisms 119 are configured to pull the anterior sections 122 toward each other and selectively lock the anterior sections 122 in proximity to each other, as will be described below. As illustrated, the tension mechanisms 119 comprise a pair of Velcro straps 124 and a corresponding pair of strap loops 126.

The superior segment 106 includes a rear portion 128, a pair of opposed arm portions 130, a tension mechanism 132, and is coupled to the rod 102 using an adjustment mechanism 134. As illustrated, the rear portion 128 and the pair of opposed arm portions 130 are again formed as a single unitary piece, which is configured to wrap around and conform to a thoracic region of the patient during use, as will be described below.

The rear portion 128 extends laterally away from the rod 102. The rear portion 128 is configured to conform to the back of the thoracic region of the patient. The pair of opposed arm portions 130 extend from opposing lateral sides of the rear portion 128. The pair of opposed arm portions 130 are each configured to conform to a corresponding lateral side of the thoracic region of the patient. The tension mechanism 132 is selectively coupled to both of the pair of opposed arm portions 130 and is configured to pull the pair of opposed arm portions 130 toward each other to selectively provide a compressive force onto the lateral sides of the patient, as will be described below. Again, the tension mechanism 132 comprises a Velcro strap 135 and a corresponding strap loop 136.

In some instances, either of the pair of opposed arm portions 130 may further include a removable pad, similar to the removable pad 121. In some instances, the removable pad may be included to improve comfortability of the back brace 100. In some other instances, the removable pad may have a thickness selected to provide a desired anterior-posterior spinal curvature correction force. Accordingly, the removable pad may comprise a combination of a stiff foam layer and a soft foam layer. The removable pad can further comprise a heating and/or a cooling layer, which can be configured too either retain heat within the back brace 100, or transfer heat out of the back brace 100, as desired.

The adjustment mechanism 134 includes an adjustment plate 137 and an adjustment band 138. The adjustment plate 137 includes a plurality of adjustment apertures 140, configured to be used in conjunction with the superior segment connection apertures 110 to selectively couple the adjustment plate 137 to the rod 102. As illustrated, the adjustment plate 137 includes a matrix of adjustment apertures 140 including three horizontal rows and seven vertical columns for a total of twenty-one adjustment apertures 140. In some instances, the adjustment plate 137 can include more or less horizontal rows and/or vertical columns of adjustment apertures 140 to provide adequate adjustability, depending on the need and/or expected growth of the patient over the term of treatment. For example, the adjustment plate 137 can include as many as five rows and as many as twenty columns for a total of one hundred adjustment apertures 140.

The adjustment band 138 is rigidly fixed to the adjustment plate 137 proximate a center of the adjustment band 138. The adjustment band 138 extends laterally from the adjustment plate 137 and partially around a periphery of the superior segment 106, and is rigidly fixed at each end to the pair of opposed arm portions 130 of the superior segment 106.

Now that the general structure of the back brace 100 has been described above, an exemplary method of use will be described below. It should be appreciated that the following description is given as an example only and is in no way meant to be limiting.

During treatment, a patient is first x-rayed to measure a pre-treatment curvature of the spine. Using the pre-treatment curvature measurements, the doctor or physician can determine an amount of adjustment necessary to correct the curvature. Once the doctor has determined the amount of adjustment necessary, the back brace 100 can be put onto the patient such that the inferior segment 104 is disposed on the pelvic region of the patient, and the superior segment 106 is disposed on the thoracic region of the patient. The inferior segment 104 can then be locked onto the pelvic region by threading the Velcro straps 124 of the tension mechanisms 119 through the strap loops 126, and pulling the pair of opposed arm portions 118 toward each other. As the pair of opposed arm portions 118 are pulled toward each other, the inferior segment 104 compresses around the pelvic region of the patient, thereby stabilizing the pelvic region of the patient.

After the pelvic region has been stabilized, the doctor can apply the determined amount of adjustment to the spine curvature by rigidly coupling the superior segment 106 to the rod 102 in a desired alignment, relative to the inferior segment 104. The plurality of adjustment apertures 140 on the adjustment plate 137 and the plurality of superior segment connection apertures 110 on the rod 102 allow the doctor to selectively rigidly couple the superior segment 106 in a variety of differing horizontal and vertical locations by using the fasteners 115 to couple pre-selected superior segment connection apertures 110 of the rod 102 to pre-selected adjustment apertures 140 of the adjustment plate 137. These pre-selected apertures 110, 140 are determined based on the desired alignment.

Once the superior segment 106 is rigidly coupled to the rod 102, the superior segment 106 can be tightened onto the patient using the tension mechanism 132, by threading the Velcro straps 135 through the corresponding strap loop 136, and pulling the pair of opposed arm portions 130 toward each other. As the pair of opposed arm portions 130 are pulled toward each other, the superior segment 106 compresses around the thoracic region of the patient, thereby locking the superior segment 106 relative to the thoracic region of the patient. Specifically, with the superior segment 106 rigidly coupled to the rod 102 in the desired alignment, as the pair of opposed arm portions 130 are pulled toward each other, one of the pair of opposed arm portions 130 applies pressure to a lateral side of the patient in the thoracic region, thereby providing the necessary spinal curvature correction force.

As such, the superior segment 106 is selectively adjustable, such that the superior segment 106 can be selectively moved and fixedly positioned in a plurality of positions along the lateral direction and the vertical direction. The plurality of positions are designed for periodic adjustment of the corrective force on the spinal curvature of the patient during the treatment period.

It should be noted that this adjustability of the superior segment 106, relative to the inferior segment 104, allows for the doctor to periodically shift the alignment of the superior segment 106, relative to the inferior segment 104, thereby allowing for treatment updates throughout a treatment period, while using the same back brace 100 throughout the treatment period. As such, this adjustability allows for the doctor to adjust the back brace 100 based on both the growth of the patient, as well as changes in the spinal curvature, over time. Thus, in addition to preventing the spinal curvature of a patient from increasing, this adjustability allows for the back brace 100 to treat and reduce the spinal curvature over time.

Figure 4C:
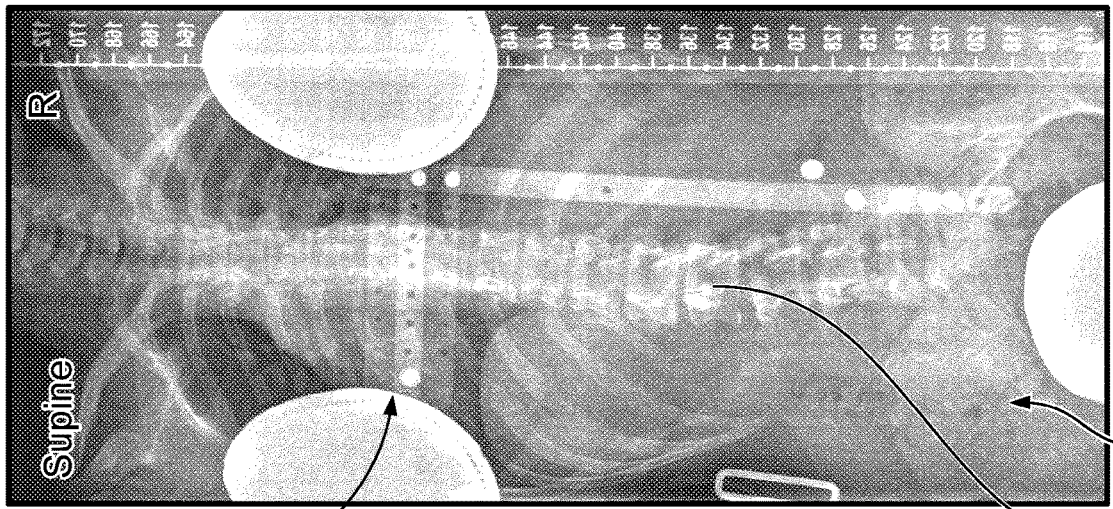
FIG. 4c is an x-ray image of the patient's spinal column while in a supine position, showing a further reduced curvature of the spine.
Figure 4B:
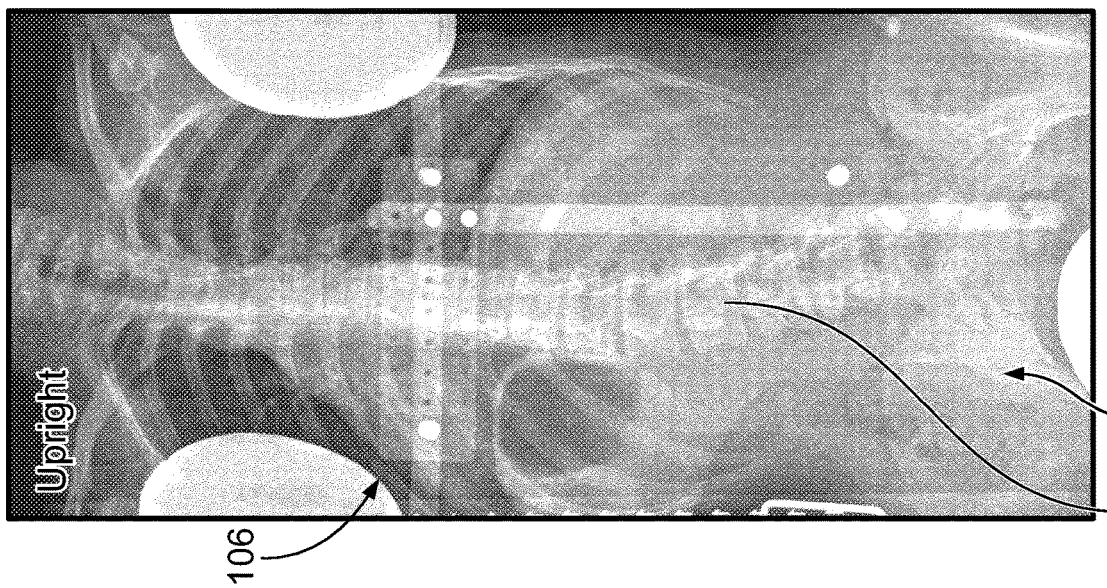
FIG. 4b is an x-ray image of the patient's spinal column while standing upright wearing the adjustable back brace of FIG. 1, showing a reduced curvature of the spine.
Figure 4A:
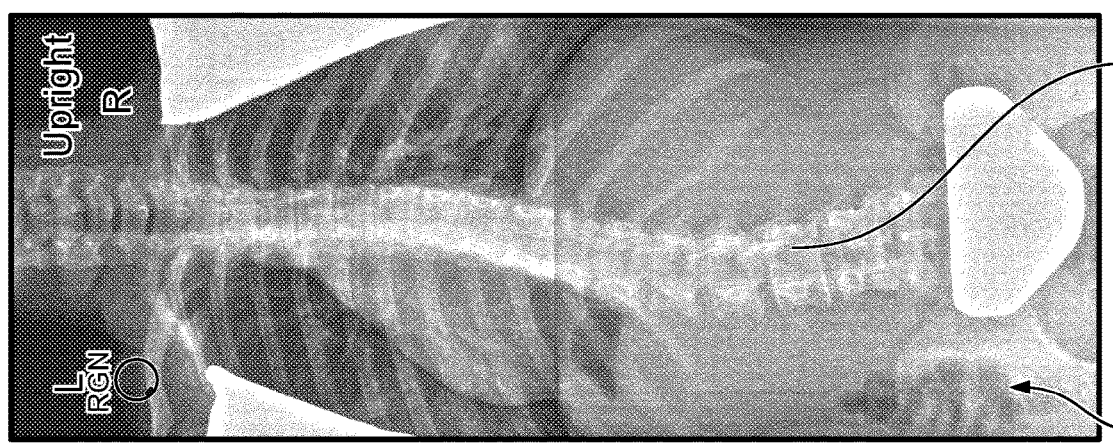
FIG. 4a is an x-ray image of a patient's spinal column while standing upright, showing a curvature of the spine.

Referring now to FIGS. 4a-4c, x-rays of a patient 400 being treated using the back brace 100 are shown. The x-ray of FIG. 4a shows the patient 400 before treatment, with the spine 402 having a spinal curvature. The x-ray of FIG. 4b shows the patient 400 wearing the back brace 100 standing upright with the superior segment 106 providing the corrective force to the spine to correct the spinal curvature. The x-ray of FIG. 4c shows the patient 400 wearing the back brace 100 laying in a supine position with the superior segment 106 providing the corrective force to the spine 402 to correct the spinal curvature. As can be seen, the back brace 100 successfully reduces the spinal curvature of the patient 400.

In some instances, it may be beneficial to provide a third segment to provide an extra point of pressure when correcting severe spinal curvature. Specifically, while stabilizing the pelvic region, applying pressure to both the lumbar and the thoracic regions of the patient may allow for more efficient treatment of the patient.

Figure 5:
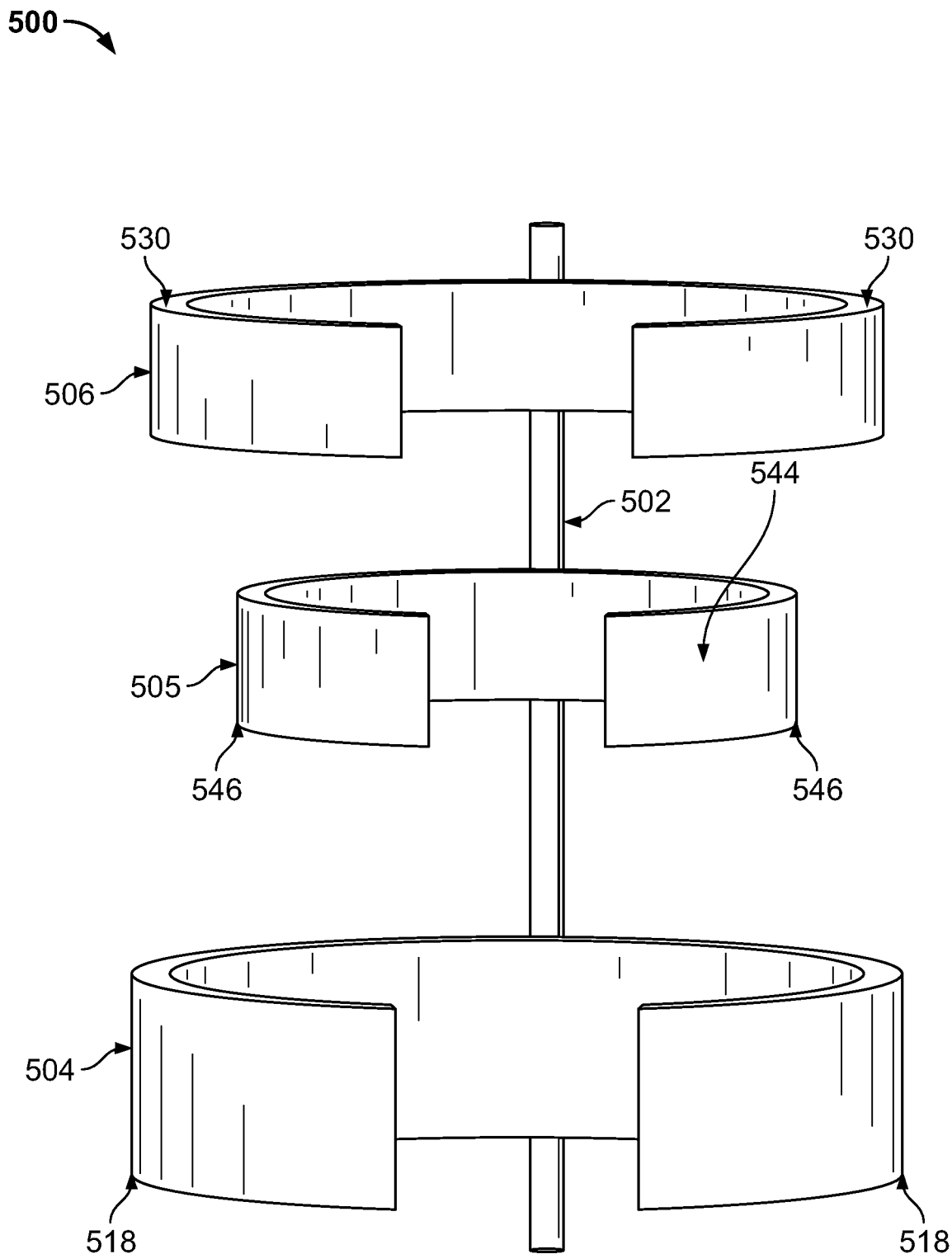
FIG. 5 is a front elevational view of another adjustable back brace in accordance with the present disclosure.
Figure 6:
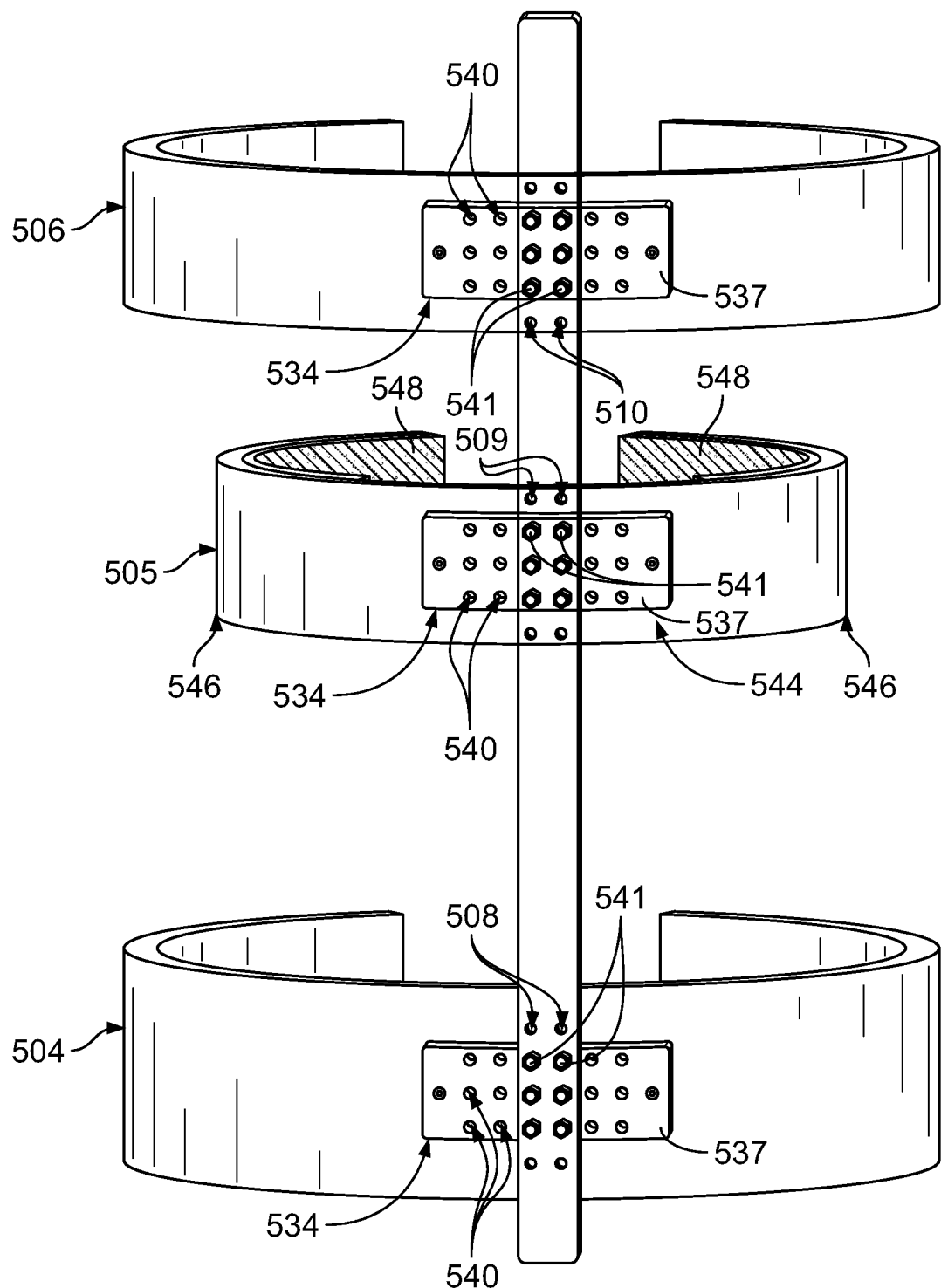
FIG. 6 is a rear elevational view of the adjustable back brace of FIG. 5.

Turning now to FIGS. 5 and 6, a back brace 500 is illustrated for correcting scoliosis of a patient. The back brace 500 is substantially similar to the back brace 100, and as such, like parts will be labeled similarly (i.e., rod 102 and rod 502, inferior segment 104 and inferior segment 504, etc.). The differences between the back brace 500 and the back brace 100 will be described below.

The back brace 500 similarly includes a rod 502, an inferior segment 504, and a superior segment 506, but additionally includes a middle segment 505.

As such, the rod 502 can include a plurality of middle segment connection apertures 509 in addition to the inferior segment connection apertures 508 and the superior segment connection apertures 510. The middle segment connection apertures 509 can be disposed proximate a center of the rod 502 can be used to couple the rod 502 to the middle segment 505. In some instances, the rod 502 can include a plurality of universal apertures disposed evenly along the length of the rod 502, which can interchangeably be used as the inferior, middle, and superior segment connection apertures 508, 509, 510, as desired.

As illustrated, the inferior segment 504 has a shorter vertical length than the inferior segment 104, and further does not include the anterior sections 122 of the back brace 100.

Further, each of the inferior segment 504, the middle segment 505, and the superior segment 506 of the back brace 500 are substantially similar in shape and function to the superior segment 106 of the back brace 100, with slight variations in shape to adequately conform each segment 504, 505, 506 to the corresponding region of the patient. Specifically, the inferior segment 504 is configured to conform to the pelvic region of the patient, the middle segment 505 is configured to conform to the lumbar region of the patient, and the superior segment 506 is configured to conform to the thoracic region of the patient.

As such, the middle segment 505 similarly includes a rear portion 544 and a pair of opposed arm portions 546, which are substantially similar to the rear portion 128 and the pair of opposed arm portions 130, respectively, of the superior segment 106.

Additionally, each of the inferior segment 504, the middle segment 505, and the superior segment 506 include an adjustment mechanism 534 substantially similar to the adjustment mechanism 134. As such, the adjustment mechanisms 534 each include an adjustment plate 537 having a plurality of adjustment apertures 540 configured to be coupled to any of the inferior, middle, and superior segment connection apertures 508, 509, 510 using fasteners 541. As illustrated, the adjustment plates 537 include a matrix of adjustment aperture 540 including three horizontal rows and six vertical columns for a total of eighteen adjustment apertures 540. However, similar to the adjustment plate 137 of the adjustment mechanism 134, in some instances, the adjustment plate 537 can include as many as five rows and as many as twenty columns for a total of one hundred adjustment apertures 540 to provide adequate adjustability, as desired.

Each of the inferior, middle, and superior segments 504, 505, 506 can additionally include tension mechanisms (not shown) similar to the tension mechanisms 119, 132 of the back brace 100. The tension mechanisms can be used to lock each of the inferior, middle, and superior segments 504, 505, 506 to the patient during treatment, as will be described below.

Additionally, as illustrated in FIG. 6, each of the inferior, middle, and superior segments 504, 505, 506 may include a removable pad 548, similar to the removable pad 121. Similarly, in some instances, the removable pad 548 may be included to improve comfortability of the back brace 500. In some other instances, the removable pad 548 has a thickness selected to provide a desired anterior-posterior spinal curvature correction force. Accordingly, the removable pad 548 can comprise a combination of a stiff foam layer and a soft foam layer. The removable pad 548 can further comprise a heating and/or a cooling layer, which can be configured to either retain heat within the back brace 500, or transfer heat out of the back brace 500, as desired.

Now that the general structure of the back brace 500 has been described above, an exemplary method of use will be described below. It should again be appreciated that the following description is given as an example only and is in no way meant to be limiting.

During treatment, a patient is first x-rayed to measure a pre-treatment curvature of the spine. Using the pre-treatment curvature measurements, the doctor or physician can determine an amount of adjustment necessary to correct the curvature of both the lumbar and thoracic spinal regions. Once the doctor has determined the amount of adjustment necessary, the back brace 500 can be put onto the patient such that the inferior segment 504 is disposed on the pelvic region of the patient, the middle segment 505 is disposed on the lumbar region of the patient, and the superior segment 506 is disposed on the thoracic region of the patient. The inferior segment 504 can then be locked onto the pelvic region using the tension mechanism (not shown), as described above with reference to the tension mechanism 119 of the inferior segment 104, to pull the pair of opposed arm portions 518 toward each other. As the pair of opposed arm portions 518 are pulled toward each other, the inferior segment 504 compresses around the pelvic region of the patient, thereby stabilizing the pelvic region of the patient.

After the pelvic region has been stabilized, the doctor can apply the determined amount of adjustment to the thoracic spinal curvature by rigidly coupling the superior segment 506 to the rod 502 in a desired alignment, relative to the inferior segment 504. The plurality of adjustment apertures 540 on the adjustment plate 537 and the plurality of superior segment connection apertures 510 on the rod 502 allow the doctor to selectively rigidly couple the superior segment 506 in a variety of differing horizontal and vertical locations by using fasteners 541 to couple pre-selected superior segment connection apertures 510 of the rod 502 to pre-selected adjustment apertures 540 of the adjustment plate 537. These pre-selected apertures 510, 540 are determined based on the desired alignment.

Once the superior segment 506 is rigidly coupled to the rod 502, the superior segment 506 can similarly be tightened onto the patient using the tension mechanism, as described above with reference to the tension mechanism 132, to pull the pair of opposed arm portions 530 toward each other. As the pair of opposed arm portions 530 are pulled toward each other, the superior segment 506 compresses around the thoracic region of the patient, thereby locking the superior segment 506 relative to the thoracic region of the patient. Additionally, with the superior segment 506 rigidly coupled to the rod 502 in the desired alignment, as the pair of opposed arm portions 530 are pulled toward each other, one of the pair of opposed arm portions 530 applies pressure to a lateral side of the patient in the thoracic region, thereby providing a corrective force to the thoracic spinal curvature.

Similarly, after the pelvic region has been stabilized and the superior segment 506 has been attached to both the thoracic region of the patient and the rod 502, the doctor can apply the determined amount of adjustment to the lumber spinal curvature by first rigidly coupling the middle segment 505 to the rod 502 in a desired middle segment alignment, relative to both the inferior segment 504 and the superior segment 506, as described above, with reference to the superior segment 506. Again, the plurality of adjustment apertures 540 on the adjustment plate 537 and the plurality of middle segment connection apertures 509 on the rod 502 allow the doctor to selectively rigidly couple the middle segment 505 in a variety of differing horizontal and vertical locations by using fasteners 513 to couple pre-selected adjustment apertures 540 of the adjustment plate 537. These pre-selected apertures 509, 540 are similarly determined based on the desired middle segment alignment.

The doctor can then tighten the middle segment 505 around the lumbar region of the patient. As the middle segment 505 is tightened around the lumbar region of the patient, as the pair of opposed arm portions 546 are pulled toward each other, one of the pair of opposed arm portions 546 applies pressure to a lateral side of the patient in the lumbar region, opposite the lateral side having pressure applied thereon by the superior segment 506, thereby providing a secondary corrective force to the lumbar spinal curvature.

As such, both the middle segment 505 and the superior segment 506 are selectively adjustable, such that the middle segment 505 and the superior segment 506 can both individually be selectively moved and fixedly positioned in a plurality of positions along the lateral direction and the vertical direction. The plurality of positions are designed for periodic adjustment of the corrective forces on the thoracic and lumbar spinal curvature of the patient during the treatment period.

It should be noted that, in addition to the benefits provided by the two-segment back brace 100, the three-segment back brace 500 provides improved treatment capabilities by allowing the doctor to individually target curvatures of both the lumbar and thoracic regions, individually. By individually targeting curvatures of both the lumbar and thoracic regions, multi-directional spinal correction is possible. Again, because the back brace 500 can be adjusted during the treatment period, the back brace 500 is not only capable of preventing the spinal curvature from increasing over time, but can further treat and reduce the spinal curvature over time.

It should also be noted that, in some instances, the various segments 104, 106, 504, 505, 506 can be made of a rigid polymer material, such as for example, a rigid copolymer. In some instances, the rods 102, 502, the adjustable plates 137, 537, and the adjustable bands 138, 538 can be made of a metallic material, such as aluminum. However, it is preferable for the entirety of both back braces 100, 500 to be made of a radio-transmissive material, as they both must be used while taking x-rays of the patient's spine, and should not obstruct the doctor's or the prosthetist's view of the spine.

In some instances, the various segments 104, 106, 504, 505, 506 may additionally include a plurality of holes to provide breathability or airflow to the patient while using either of the corresponding back braces 100, 500.

Further, because the inferior segment, the middle segment, and the superior segment are made separately, the three segments can be replaced as desired throughout treatment period, as desired, to better conform to the patient as they grow or their body shape changes throughout the treatment period, which can last between five and ten years, and in some cases, even longer. This capability of the segments to be replaced allows for more accurate treatment of the patient throughout the treatment period.

Additionally, because the various segments are provided separately, they can be commercially produced in generic sizes and assembled by the doctor or prosthetist to match the patient's pelvic, lumbar, and thoracic regions, as necessary, removing the need for the back braces 100, 500 to be individually made per patient.

Although the above-described methods of use are in reference to correcting a curvature of the spine due to scoliosis, the back braces 100, 500 can additionally be applied in similar fashion to treat children and adults that have been in accidents, need upper torso rehabilitation, or have a need for a brace that can be quickly made and customized to their specific needs.

As such, the present disclosure provides a back brace comprising two or three individual segments that can target curves in the thoracic and lumbar regions of the spine and stabilize the pelvic region more efficiently than currently available back braces. The multi-piece brace can additionally offer more adjustability than a typical one-piece design.

Further, it will be appreciated that, while the back braces disclosed herein include two or three individual segments, the back braces can include more individual segments to accurately target additional curves in the thoracic and lumbar regions, as desired or deemed necessary by a doctor or prosthetist.

The back brace disclosed herein can additionally be generically made and assembled by a doctor and or prosthetist. As such, the back brace does not need to be individually made per patient, providing a reduction in lead time. The back brace can also be adjusted throughout a treatment period of the patient to account for growth and changes in spinal curvature over time, allowing the back brace to account for the dynamic growth of younger patients with spinal disorders, resulting in a more accurate correction of spinal curvature. The versatility of the disclosed multi-piece back brace will improve the quality of treatment, health, and life for a scoliosis patient.

The present invention has been described in terms of one or more preferred embodiments, and it should be appreciated that many equivalents, alternatives, variations, and modifications, aside from those expressly stated, are possible and within the scope of the invention.

The invention claimed is:

1. A back brace configured to aid in the correction of spinal curvature during a treatment period of a patient, the back brace comprising:
   a rod configured to extend along a vertical direction oriented along a patient;
   an inferior segment coupled to the rod, extending in a lateral direction from the rod, and configured to at least partially wrap around and conform to the patient during use, the inferior segment being further configured to apply pressure to both a first lateral side and a second lateral side of the patient proximate a pelvic region of the patient, thereby stabilizing the pelvic region of the patient relative to the rod;

a superior segment adjustably coupled to the rod above the inferior segment, extending in a lateral direction from the rod, and configured to at least partially wrap around and conform to the patient during use, the superior segment being further configured to apply pressure to one of the first lateral side and the second lateral side of the patient, proximate a thoracic region of the patient, to provide a corrective force on the spinal curvature of the patient;

a first adjustment plate configured to adjustably couple the inferior segment to the rod at differing vertical and horizontal locations, the first adjustment plate including a plurality of adjustment apertures and the rod including a first plurality of connection apertures, the first adjustment plate configured to be coupled to the rod using at least one fastener to couple at least one adjustment aperture of the first adjustment plate to at least one connection aperture of the first plurality of connection apertures; and a second adjustment plate configured to adjustably couple the superior segment to the rod at differing vertical and horizontal locations, the second adjustment plate including a plurality of adjustment apertures and the rod including a second plurality of connection apertures, the second adjustment plate configured to be coupled to the rod using at least one fastener to couple at least one adjustment aperture of the second adjustment plate to at least one connection aperture of the second plurality of connection apertures, wherein the superior segment is selectively adjustable, such that the superior segment can be selectively moved and fixedly positioned in a plurality of positions along at least one of the lateral direction or the vertical direction, wherein the plurality of positions are designed for periodic adjustment of the corrective force on the spinal curvature during the treatment period, wherein each of the inferior segment and the superior segment includes a rear portion extending laterally away from the rod and a pair of opposed arm portions extending away from opposing lateral sides of the rear portion in an anterior direction, wherein, for each of the inferior segment and inferior segment, one arm portion of the pair of opposed arm portions applies a variable pressure to the first lateral side of the patient that can be varied via a move of the respective adjustment plate in the lateral direction relative to the rod, and the other arm portion of the pair of opposed arm portions applies a variable pressure to the second lateral side of the patient that is varied via the move of the respective adjustment plate in the lateral direction relative to the rod, and wherein the first lateral side and the second lateral side of the patient are on opposing sides of the patient.

2. The back brace of claim 1, further comprising a middle segment adjustably coupled to the rod between the inferior segment and the superior segment and configured to at least partially wrap around and conform to the patient during use, the middle segment being further configured to apply pressure to another one of the first lateral side and the second lateral side of the patient, proximate a lumbar region of the patient, opposite the one of the first lateral side and the second lateral side having pressure applied thereon by the superior segment to provide an additional corrective force on the spinal curvature of the patient.

3. The back brace of claim 2, wherein the middle segment is selectively adjustable, such that the middle segment can be selectively moved and fixed positioned in another plurality of positions along at least one of the lateral direction of the vertical direction, wherein the another plurality of positions are designed for periodic adjustment of the additional corrective force on the spinal curvature of the patient during the treatment period.

4. The back brace of claim 2, wherein at least one of the inferior segment, the middle segment, and the superior segment includes a removable pad on an interior surface, wherein the removable pad has a thickness selected to provide an anterior-posterior spinal curvature correction force.

5. The back brace of claim 2, wherein the middle segment includes a third adjustment plate configured to adjustably couple the middle segment to the rod.

6. The back brace of claim 1, wherein the plurality of adjustment apertures of the first and second adjustment plates are arranged in a matrix having a plurality of horizontal rows and a plurality of vertical rows.

7. The back brace of claim 2, wherein the middle segment includes a rear portion extending laterally away from the rod and a pair of opposed arm portions extending away from opposing lateral sides of the rear portion in an anterior direction.

8. The back brace of claim 7, wherein each of the inferior segment, the middle segment, and the superior segment includes a tension mechanism configured to pull the pair of opposed arm portions toward each other.

9. A method for correcting spinal curvature of a patient with a back brace including a rod, an inferior segment coupled to the rod, and a superior segment adjustably coupled to the rod above the inferior segment, the method comprising:

securing the inferior segment to a pelvic region of the patient to stabilize a pelvic region of the patient relative to the rod via an adjustment plate, the inferior segment including a rear portion extending laterally away from the rod and a pair of opposed arm portions extending away from opposing lateral sides of the rear portion in an anterior direction, thereby applying pressure to each of opposing first and second lateral sides of the patient, the adjustment plate including a plurality of adjustment apertures and the rod including a plurality of connection apertures, the adjustment plate configured to be coupled to the rod using at least one fastener to couple at least one adjustment aperture to at least one connection aperture at differing horizontal and vertical locations;

placing the superior segment around a thoracic region of the patient;

subsequent to placing the superior segment around the thoracic region of the patient, rigidly coupling the superior segment to the rod in a desired alignment, relative to the inferior segment;

subsequent to rigidly coupling the superior segment to the rod in the desired alignment, tightening the superior segment around the thoracic region of the patient, thereby applying a pressure to each of the first and second lateral sides of the thoracic region of the patient; and adjusting the horizontal location of the superior segment adjustment plate relative to the rod to adjust the pair of opposed arms of the superior segment and the pressure applied to each of the first and second lateral sides of the thoracic region of the patient by the pair of opposed arm, wherein the desired alignment is predetermined to apply a corrective force to the spinal curvature of the patient when the superior segment is tightened around the thoracic region of the patient.

10. The method of claim 9, wherein the back brace additionally includes a middle segment adjustably coupled to the rod between the inferior segment and the superior segment.

11. The method of claim 10, further comprising:

placing the middle segment around a lumbar region of the patient;

subsequent to placing the middle segment around the lumbar region of the patient, rigidly coupling the middle segment to the rod in a desired middle segment alignment, relative to the inferior segment;

subsequent to rigidly coupling the middle segment to the rod in the desired middle segment alignment, tightening the middle segment around the lumbar region of the patient, thereby applying pressure to one of the first lateral side and the second lateral side of the lumbar region of the patient opposite the one of the first lateral side and the second lateral side of the patient having pressure applied thereon by the superior segment; and wherein the desired middle segment alignment is predetermined to apply a secondary corrective force to the spinal curvature of the patient when the middle segment is tightened around the lumbar region of the patient.

12. The method of claim 11, wherein at least one of the middle segment and the superior segment is selectively adjustable, such that the at least one of the middle segment and the superior segment can be selectively moved in either of a lateral direction and a vertical direction, with respect to the inferior segment, allowing for periodic adjustment of the back brace during the treatment period.

* * * * *